US008348878B2

(12) United States Patent
Black et al.

(10) Patent No.: US 8,348,878 B2
(45) Date of Patent: Jan. 8, 2013

(54) DEVICE FOR DISPENSING CREAM LADEN GAUZE

(75) Inventors: Eric L Black, Mount Vernon, IL (US); David S Asbery, Mount Vernon, IL (US)

(73) Assignee: AB Holdings, LLC, Mt. Vernon, IL (US)

( * ) Notice: Subject to any disclaimer, the term of this patent is extended or adjusted under 35 U.S.C. 154(b) by 396 days.

(21) Appl. No.: 12/617,781

(22) Filed: Nov. 13, 2009

(65) Prior Publication Data

US 2011/0114640 A1    May 19, 2011

(51) Int. Cl.
*A61F 13/20*    (2006.01)
*B65D 1/24*    (2006.01)
*A47K 10/24*    (2006.01)
*B65H 1/00*    (2006.01)
*G07F 11/00*    (2006.01)
*A47F 1/00*    (2006.01)

(52) U.S. Cl. ............. 604/13; 604/11; 220/500; 221/45; 221/96; 221/97

(58) Field of Classification Search .................... 604/11, 604/13, 20, 19, 289, 304–308, 310, 515; 220/500; 221/1, 45, 96, 97; 206/440; 202/500
See application file for complete search history.

(56) References Cited

U.S. PATENT DOCUMENTS

| | | | | |
|---|---|---|---|---|
| 3,995,582 A * | 12/1976 | Douglas | .......................... | 118/43 |
| 4,406,730 A | 9/1983 | Altmix | .......................... | 156/574 |
| 5,032,109 A * | 7/1991 | Sibalis | .......................... | 604/20 |
| 5,263,927 A * | 11/1993 | Shlain | .......................... | 604/13 |
| 5,651,768 A * | 7/1997 | Sibalis | .......................... | 604/20 |
| 6,662,967 B2 | 12/2003 | Roy | .......................... | 221/58 |
| 7,056,385 B2 * | 6/2006 | Likosar | .......................... | 118/249 |
| 7,133,717 B2 * | 11/2006 | Coston et al. | .......................... | 604/20 |
| 2003/0088204 A1 * | 5/2003 | Joshi | .......................... | 604/20 |
| 2006/0051865 A1 * | 3/2006 | Higgins et al. | .......................... | 435/366 |
| 2006/0278588 A1 * | 12/2006 | Woodell-May | .......................... | 210/787 |
| 2008/0114284 A1 * | 5/2008 | Anderson et al. | .......................... | 604/20 |

* cited by examiner

*Primary Examiner* — Tatyana Zalukaeva
*Assistant Examiner* — Benjamin Klein
(74) *Attorney, Agent, or Firm* — Carla Gannon Law

(57) ABSTRACT

A dispensing device deposits cream onto a strip of gauze by housing a roll of gauze that is unrolled and pulled through a user-fillable reservoir of cream. The amount of cream deposited on the gauze is regulated by applying pressure to various parts of the device. Cream laden gauze is then used in the conventional manner.

2 Claims, 5 Drawing Sheets

DEVICE FOR DISPENSING CREAM LADEN GAUZE

FIELD OF THE INVENTION AND BACKGROUND

The present invention relates generally to drug dispensing devices and, more particularly, to a device that produces and dispenses a strip of cream laden gauze from the gauze and cream contained therein.

In the medical field, there are many uses for cream-laden gauze or other cream-laden non-woven permeable materials. These types of combination products are useful in the treatment of skin wounds or abrasions in humans or animals by wrapping the damaged area with a gauze bearing a medicated cream. For example, cream laden gauze wrap for such external use might contain an antibiotic or debridement agent, a hemostatic substance to stop bleeding or other medicinal agents which would be positioned on a wound and subsequently covered with a bandage or dry gauze wrap. Such gauze wraps are frequently used to treat or prevent infections or other adverse events at damaged areas occurring on the extremities, the neck, head, torso or other body locations. Such cream laden gauze products are also used to form packs or plugs of such a combination gauze-with-medicated cream product to create pressure to stop bleeding, promote healing, or prevent or treat infections, for example. The gauze packs are used to provide certain medical benefits by inserting them into the body cavities of the body of man or animals, or into injury-caused or surgically-caused crevices, holes or incisions such as broken bones, cranial trepining, anal fissures such as pylenonital cysts, various rectal surgical procedures such as hemorrhoidal repair, or for posterior nosebleeds, and vaginal surgical procedures such as hysterectomy, vaginal floor or wall repair or reconstruction, cystocele repair and other gynecological surgical procedures.

Approximately 650,000 hysterectomies are performed each year in the United States alone. This equates to approximately 8 out of 1,000 women per year. The rate is similar in Canada, but lower in Europe and Asia, where they are performed on about 3 in 1,000 per year. At the conclusion of many hysterectomies it is desirable to stop the blood-vessel rich vaginal wall from bleeding, and to promote new tissue growth. This is conventionally accomplished with a vaginal "gauze pack" inserted immediately post-surgery while the patient is still in the operating room. Vaginal gauze packs impregnated with estrogen cream are effective because they stop bleeding via direct pressure, and promote new tissue growth due to the properties of the estrogens in the cream. Normally the gauze pack remains in the patient overnight, and is removed the next morning. Gauze packs are also used in other intravaginal procedures, including bladder prolapse surgery, interuterine fibroid surgery, and pelvic floor reconstruction.

Vaginal gauze packs are typically prepared in the operating room by a nurse or aide. They will place approximately 15' of 2" gauze in a large basin, add the contents of a an approximately 45 g tube of cream, knead the cream into the gauze, then attempt to untangle the resulting roll of cream laden gauze and fold it neatly for placement into the vaginal canal by the doctor.

The conventional methods of preparing vaginal gauze packs and other extemporaneously-prepared gauze pack or strips have substantial drawbacks. For one, it is a messy procedure that requires cleanup afterwards. Also, it is time consuming for operating room personnel. Moreover, approximately 15-20% of the cream is wasted, which is substantial considering, for example, that one 45 g of PREMARIN® bears a wholesale cost of about $90. Most importantly, however, is that cream coverage to the gauze can be non-uniform, thereby potentially lessening the positive effects of the gauze pack.

Thus, there remains a need for a new and improved device for preparing cream laden gauze, and a method for using this device. Ideally this device would be economical with respect to manufacturing and delivery. It should be simple to use, thereby reducing the time and expense in the operating room. Ideally the device is operable by one person, and this one person is able, for example, to prepare a 15' to 25' strip of cream laden gauze in approximately 30 seconds. It should also be adjustable insofar as the operator can increase or decrease the amount of cream being deposited on the gauze. The device should be disposable in non-biohazard trash, thereby decreasing clean-up costs. It should be less wasteful of cream than conventional preparation methods. Finally, it should produce cream laden gauze with uniformly deposited cream.

SUMMARY OF THE INVENTIONS

The present inventions are directed to devices that produce and dispense a strip of cream laden gauze. The major structures of the preferred embodiment can include a gauze housing, which retains a roll of gauze; and a cream reservoir, which retains a supply of cream to be deposited on the gauze. The cream reservoir can be filled by removing a plug to expose a threaded or adjustable-entry port, connecting a tube of cream to the threaded or flexible port, squeezing the tube's contents into the reservoir, then replacing the plug. The housing with the roll of gauze can be one end of the device, with the terminal end of the gauze protruding out the other end of the device. As a user pulls on the terminal end of the gauze, gauze is unrolled and travels through a first channel, then through a reservoir of cream, then through a second channel, then exits the device as cream laden gauze. The user is able to regulate the amount of cream deposited on the gauze by applying pressure to the cream reservoir and/or second channel. Cream laden gauze is then used in the conventional manner. The device is preferably disposable, and intended for single usage.

These and other aspects of the present inventions will become apparent to those skilled in the art after a reading of the following description of the preferred embodiment when considered with the drawings.

DESCRIPTION OF THE PREFERRED EMBODIMENTS

Figure 1:
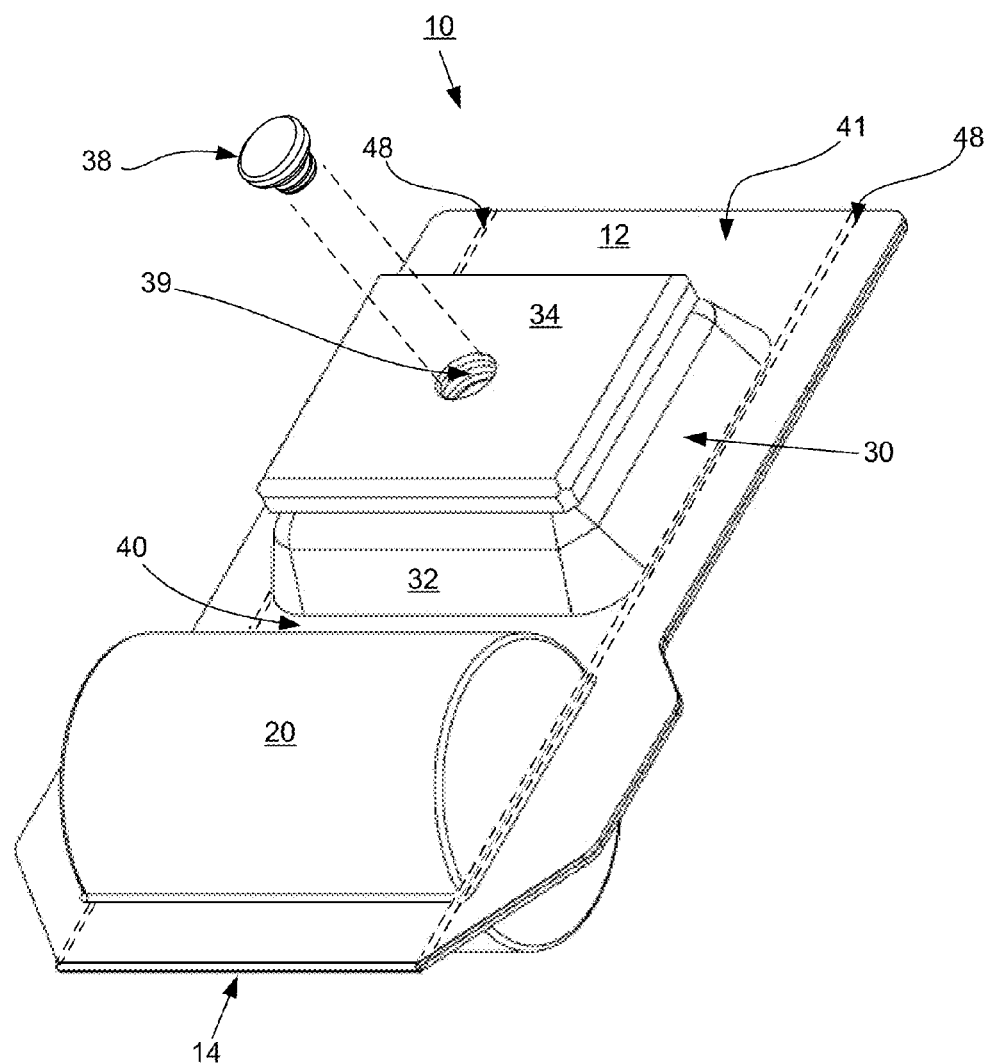
FIG. 1 is a perspective view of a dispensing device with the cap removed.

In the following description, like reference characters designate like or corresponding parts throughout the several views. It should be understood that the illustrations and descriptions are provided for the purpose of describing preferred embodiments of the inventions, but are not intended to limit the inventions thereto.

The preferred embodiment of the present invention is a dispensing device that deposits cream onto a strip of gauze. As used herein for convenience and brevity, "cream" describes a viscous or semi-solid medicinal or non-medicinal substance such as a paste, gel, emulsion, lotion, wash, soft polymer such as polyethylene glycols, or ointment, with pharmaceutical preparations being preferred. Specific medicinal substances include antibiotics, astringents, hemostats, debridements, anti-inflammatory agents, hormones, enzymes, healing promoters, and antitumor agents. Estrogen-containing products such as PREMARIN® Vaginal Cream are considered particularly suitable. As used herein for convenience and brevity, "gauze" refers to strips of medical materials such as open-weave cotton, regular-weave or knit cotton, non-textile cotton, silk, synthetic textiles, foam, tape, adhesive tapes, casting tape and strips for broken bones, and the like.

The device retains a roll of gauze in one end, with the unrolled terminal end of the gauze protruding out the other end of the device. As a user pulls on the terminal end of the gauze, unrolled gauze travels through a first channel, then a reservoir of cream, then a second channel, then exits the device as cream laden gauze. The user is able to regulate the amount of cream deposited on the gauze by applying pressure to the cream reservoir and/or second channel. Cream laden gauze is then used in the conventional manner. The device is preferably disposable, and intended for single usage.

As best seen in FIG. 1, dispensing device 10 includes two major receptacles: gauze housing 20 and cream reservoir 30. Gauze housing 20 is preferably substantially cylindrical, and sized to retain a roll of gauze approximately 2" wide and approximately 10' to 20' long, with 15' long being most desirable, although other dimensions are certainly possible. For example, ¼" wide gauze, which has applications in surgeries such rhinoplasty, to 5" or more—wide gauze, which is amenable to casting broken bones or wrapping an appendage such as a leg or arm or an abdomen or chest. Cream reservoir 30, which preferably has an internal volume of approximately 30 cc to approximately 45 cc, includes rigid plate 34, which defines port 36. Rigid plate 34 is preferably positioned externally. Preferably, port 36 includes threaded perimeter 39, and complementarily threaded plug 38. Cream reservoir preferably also includes at least one flexible wall 32.

Approximate preferred dimensions are: length of device 10 of 10"; width of widest portion of device 10 of 3.63"; length of gauze housing 20 of 2.34", width of gauze housing 20 of 1.65"; length of rigid plate 34 of 1.97"; thickness of rigid plate 34 of 0.18"; length of cream reservoir 30 of 1.97"; width of cream reservoir 30 of 2.09"; and height of cream reservoir 30 of 0.53".

Device 10 can be constructed of a variety of materials, preferably thermoplastics, which lend themselves to thin (approximately 0.007") injection molding. Suitable materials include PVC, PET, PETE, polyethylene, and polypropylene, and other polymers with PETG being most preferred. Amber, light-blocking white, or other colored plastic may be employed for light protection, or various colors may be used to identify intended drugs. Rigid plate 34 is substantially less flexible than the remainder of device 10, and can be manufactured separately and later attached. Preferably, rigid plate 34 is constructed of PVC, although ABS is also suitable. Flexible wall 32 of cream reservoir 30 is preferably thin enough (approximately 0.007") to permit downward movement of rigid plate 34 during use, thereby leading to compression of cream reservoir 30. First channel 40 and second channel 41 are formed by seams 48 running near longitudinal edges of device 10. Preferably seams 48 are formed by heat fusion, but other means such as adhesives and mechanical sealers are also possible.

Figure 2:
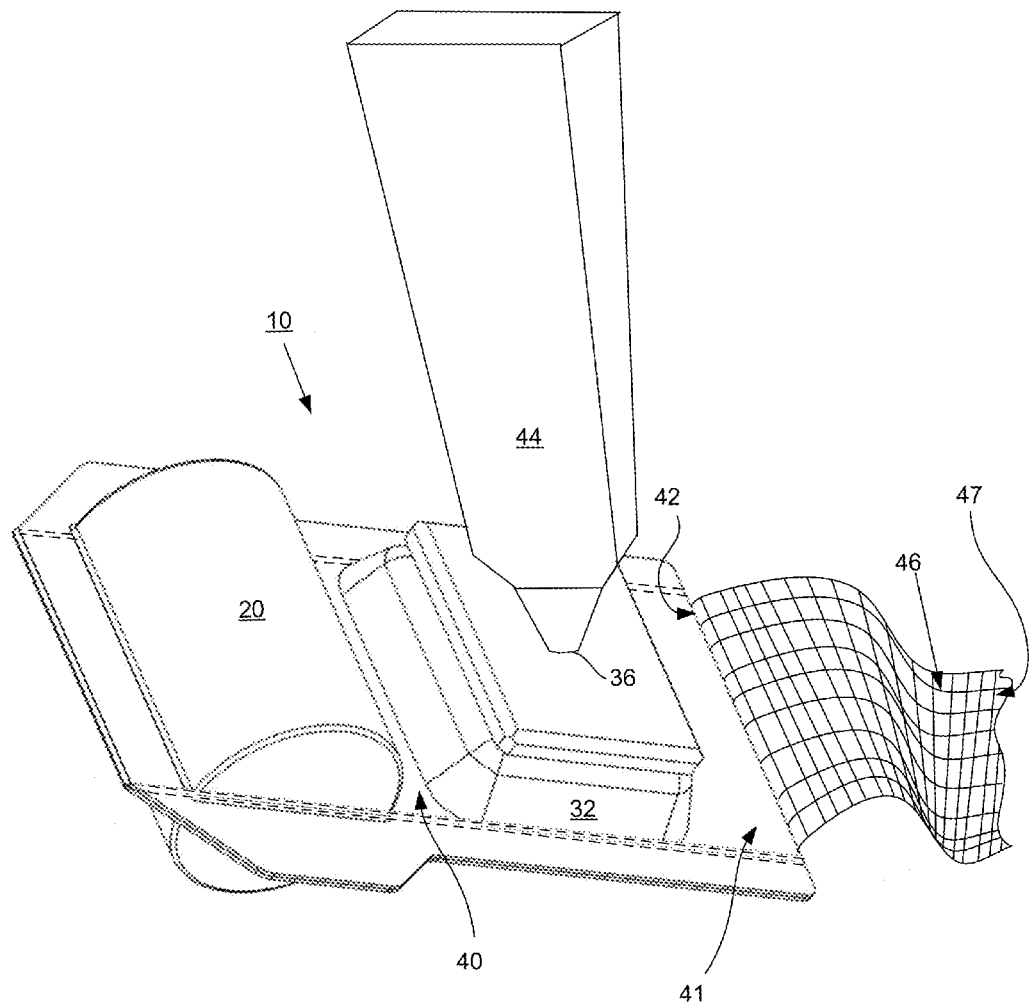
FIG. 2 is a perspective view of a dispensing device with a tube of cream connected.

Referring to FIG. 2, when cap 38 is absent, port 36 can be threadably engaged with cream tube 44.

Gauze roll 25 (shown in phantom in alternative embodiment of FIG. 6) is retained within gauze housing 20, with gauze 46 traveling along longitudinal axis of device 10 when pulled at terminal end 47. Specifically, gauze 46 from gauze roll 25 of housing 20 first passes through first channel 40, then through reservoir 30, then through second channel 41, and exits outlet 42 (best shown in alternative embodiment of FIG. 6). Accordingly, housing 20, first channel 40, reservoir 30, second channel 41 and outlet 10 are oriented linearly along the longitudinal axis of device 10, each in fluid communication one with another. Spinning gauze roll 25 is retained in housing as unrolled gauze is pulled through device 10. Preferably device 10 is manufactured and assembled such that user receives device 10 with terminal end 10 extending through outlet 42, so that it is not necessary to "fish" out gauze 46.

Gauze 46 accumulates cream 45 as it passes through reservoir 30. The amount of cream deposited can be increased by exerting downward pressure on rigid plate 34, which compresses flexible walls 32, thereby "squishing" cream 45 into weave of gauze 46. Additionally or alternatively, the amount of cream on gauze 46 can be decreased by exerting downward pressure on deformable second channel 41, thereby "wiping" cream 45 from gauze 46. Device 10 was designed to enable the operator to regulate the deposition of cream while holding the device with one hand, with the operator's other hand pulling gauze 46 through outlet 42. The cream laden gauze exiting outlet 42 is ready for conventional use, such as folding and packing wounds or surgical sites.

Figure 3:
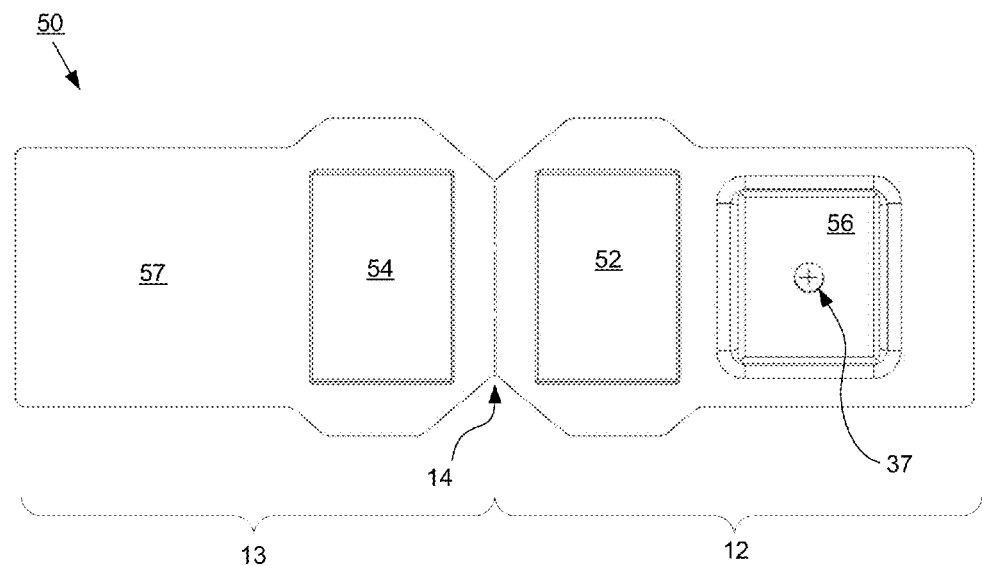
FIG. 3 is a top view of a blank for forming a dispensing device.
Figure 4:
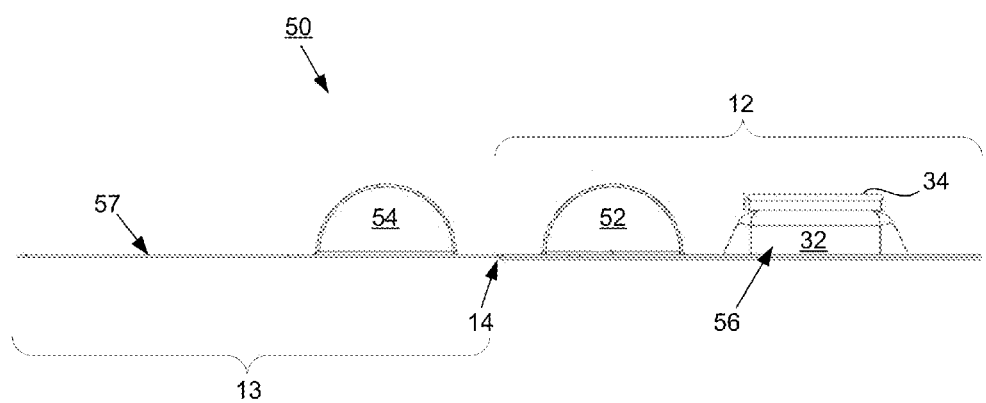
FIG. 4 is a side view of a blank for forming a dispensing device.

Referring now to FIGS. 3 and 4, device 10 can be formed from blank 50, which is preferably injection molded. Optionally, rigid plate 34 can be manufactured separately and attached to top reservoir section 56, as shown in FIG. 4. Blank 50 includes top portion 12 connected to bottom portion 13 at foldable axis 14. Upon folding, top reservoir section 56 and bottom reservoir section 57, the latter of which is preferable substantially planar, come together to collectively form cream reservoir 30. Additionally, top housing section 52 and bottom housing section 54, which are substantially similar to each other, come together to collectively form gauze housing 20, which is preferably substantially a hollow cylinder. Top reservoir section 56 preferably includes at least one flexible wall 32, and aperture 37 in alignment with port 36 of plate 34.

Figure 6:
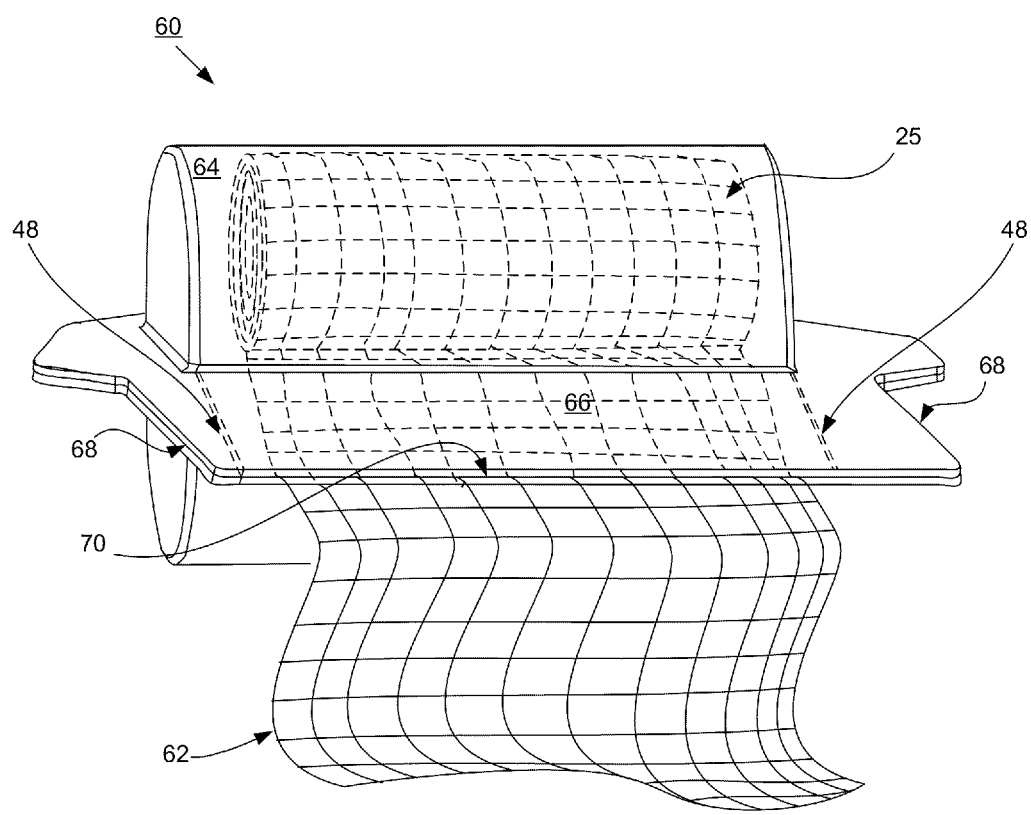
FIG. 6 is a perspective view of an alternative embodiment."

As shown in FIG. 6, another embodiment is alternative dispensing device 60, which does not include a reservoir. In this embodiment, housing 64 contains cream laden gauze 62 that is pulled through outlet 70 via deformable channel 66. The user can decrease the amount of cream by clamping down on deformable channel 66, which is substantially planar. Alternatively, the user can minimize loss of cream passing through channel 66 by squeezing edges 68, thereby widening said channel 66. It is also possible to utilize dispensing device 60 with dry gauze in housing 64, which would maintain a roll of gauze in a sterile environment during use.

Figure 5:
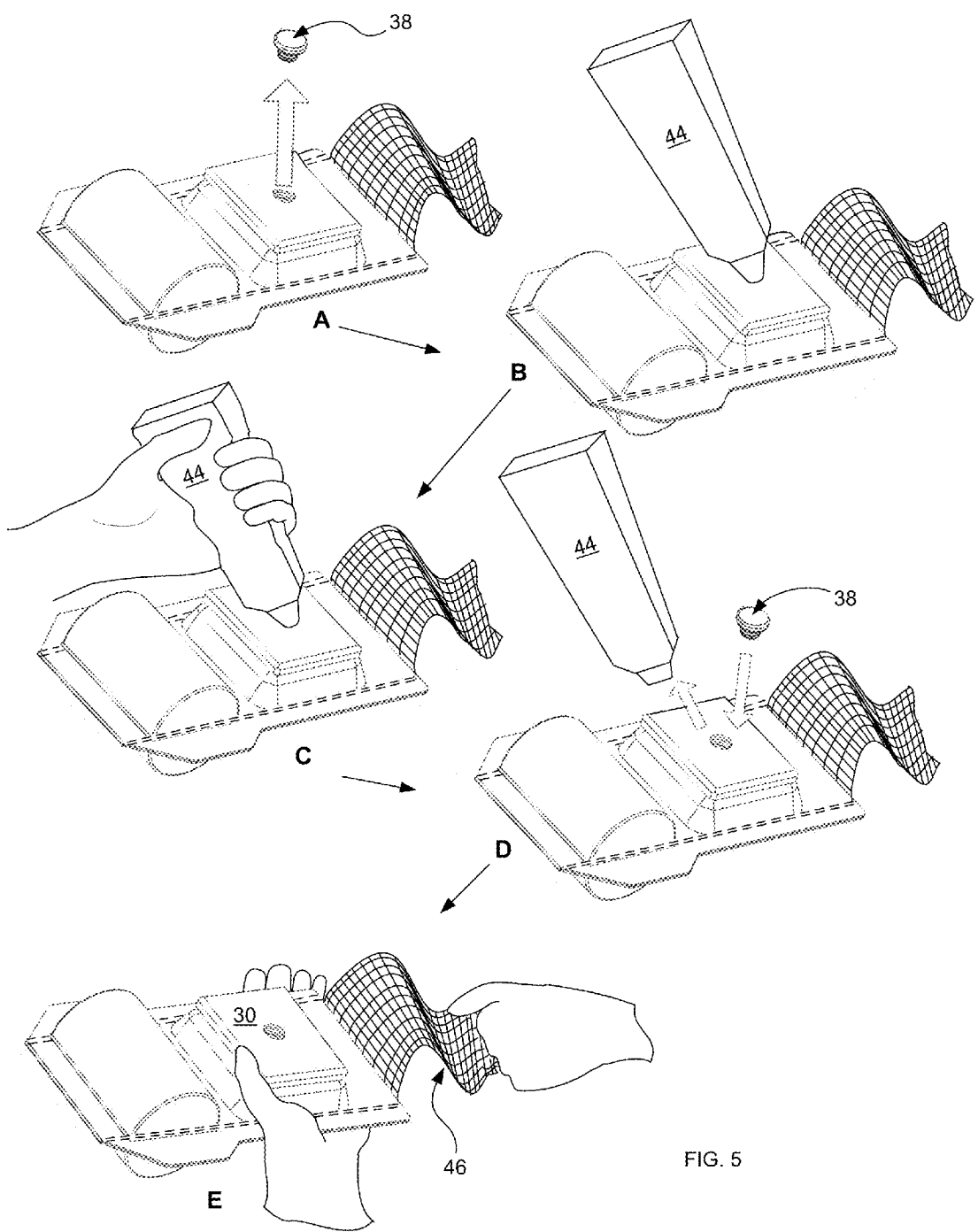
FIG. 5 schematically represents various steps in using a dispensing device including:
 A—removing a plug;
 B—connecting a tube of cream;
 C—squeezing the tube;
 D—removing the tube and replacing the plug; and
 E—squeezing the device and pulling the gauze.

Referring now to FIG. 5, device 10 is preferably used by: removing plug 38 (FIG. 5A); threadably connecting tube 44 to device (FIG. 5B); transferring cream of tube 44 by squeezing (FIG. 5C); removing tube 44 and replacing plug 38 (FIG. 5D); and compressing reservoir 30 while pulling gauze 46 (FIG. 5E). Resulting cream laden gauze is subsequently used in the conventional manner Certain modifications and improvements will occur to those skilled in the art upon a reading of the foregoing description and viewing of the foregoing figures. By way of example, it is possible to forego rigid plate 34, or position rigid plate 34 interiorly. It is possible to use more than one type of cream 45. It is possible to include a means for cutting near outlet 42, thereby permitting the preparation of multiple strips of cream laden gauze. Cutting means could be serrated edge or blade (not shown). It is possible to use device 10 to prepare cream laden gauze for external use, for example an antibiotic or other drug preparation to be positioned on a wound, and subsequently covered with a bandage. Mounting device 10 on a wall or other surface using straps, a holder or attaching means is also possible, thereby "freeing up" the hand holding the device. It is possible for device 10 to be openable and closeable, thereby permitting the replacement of gauze roll 25. It is possible for device 10 to be constructed of materials that could withstand repeated use and sterilization. It is also possible for the port to accommodate a variety of tube sizes by being deformable, including multiple "adaptor tips" of various sizes to connect the tube to the port of the device, by having a port that is adjustable, a fixed port that "funnels", pressure-opening, self-closing, or a variety of other means.

It should be understood that all such modifications and improvements have been deleted herein for the sake of conciseness and readability but are properly within the scope of the following claims.

We claim:

1. A dispensing device comprising:
   a) a gauze housing;
   b) a rolled strip of gauze within said housing, said rolled strip including a terminal end having a substantially planar orientation;
   c) a cream reservoir;
   d) cream within said reservoir, said rolled strip and said cream in fluid communication by a first channel; and
   e) a second channel in fluid communication with said cream reservoir, wherein said device is configured to allow said terminal end to travel a path from said gauze housing, to said first channel, to said cream reservoir, to said second channel, then exiting said device while cream-laden and maintaining said substantially planar orientation.

2. The dispensing device of claim 1 wherein said gauze housing is configured to permit said rolled strip of gauze to unroll upon pulling said terminal end away from said second channel.

* * * * *